United States Patent [19]

Kimura et al.

[11] 4,274,424
[45] Jun. 23, 1981

[54] DEVICE FOR AUTOMATICALLY WINDING A BLOOD PRESSURE MEASURING CUFF

[75] Inventors: Shigenobu Kimura; Yoshiro Kubo; Shigeru Bando; Akio Ose; Yukuo Kinoshita; Ryoichi Higashizono; Ikuo Hanamiya, all of Kawasaki, Japan

[73] Assignee: Fuji Electric Co., Ltd., Kawasaki, Japan

[21] Appl. No.: 46,413

[22] Filed: Jun. 7, 1979

[30] Foreign Application Priority Data

Jun. 12, 1978 [JP] Japan .................................. 53-69841

[51] Int. Cl.³ ............................................. A61B 5/02
[52] U.S. Cl. .................................................... 128/686
[58] Field of Search .................... 128/75, 327, 675–686

[56] References Cited

U.S. PATENT DOCUMENTS

| | | | |
|---|---|---|---|
| 2,940,442 | 6/1960 | Wilhelm | 128/75 |
| 3,709,217 | 1/1973 | Powers | 128/75 |
| 3,935,984 | 2/1976 | Lichowsky et al. | 128/686 |
| 4,109,646 | 8/1978 | Keller | 128/686 |
| 4,206,765 | 6/1980 | Huber | 128/677 |

FOREIGN PATENT DOCUMENTS 994147 8/1951 France ...................... 128/677
2326904 5/1977 France ...................... 128/686

Primary Examiner—Robert W. Michell
Assistant Examiner—Francis J. Jaworski
Attorney, Agent, or Firm—Sughrue, Rothwell, Mion, Zinn & Macpeak

[57] ABSTRACT

A device for automatically winding a blood pressure measuring cuff around a part of the human body. The cuff comprises a flexible band having a part fixedly secured to a surrounding member adapted to receive a part of the human body. The flexible band extends circumferentially along the inner wall of the surrounding member and having one end which is pulled circumferentially so as to be wound around a part of the human body. A flexible fluid chamber is provided along the inner wall of the flexible band to be interposed between the flexible band and a part of the human body. The flexible fluid chamber operates to apply a squeezing pressure to the part of the human body when a fluid is supplied to the flexible fluid chamber. A weight is connected to one end of the flexible band and a weight hoisting device is employed for hoisting the weight. A weight holder holds the weight at a predetermined hoisting position and a pulling force is caused by the weight when the holder is released and applied to the one end of the flexible band.

8 Claims, 3 Drawing Figures

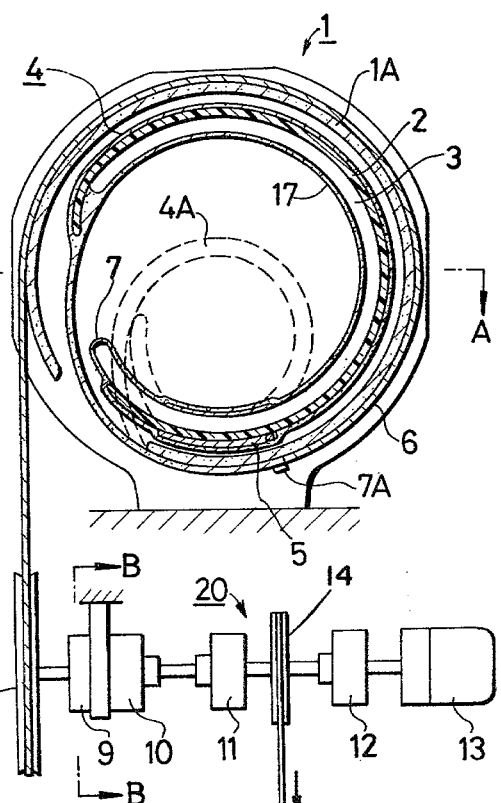
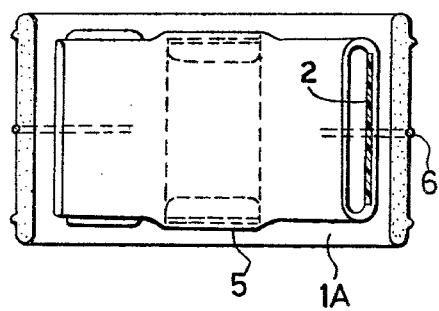
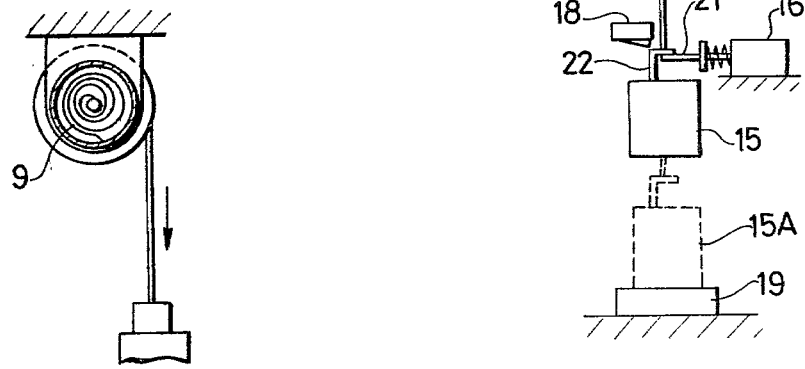
FIG. 1
FIG. 2
FIG. 3

DEVICE FOR AUTOMATICALLY WINDING A BLOOD PRESSURE MEASURING CUFF

BACKGROUND OF THE INVENTION

This invention relates to a device for automatically winding a blood pressure measuring cuff around a part of the human body such as an arm, for blood pressure measurement.

In general, for blood pressure measurement, the blood pressure measuring cuff is wound around the upper arm in such a manner that the central part of an air bag made of rubber (hereinafter referred to as "a rubber bag" when applicable) is on the upper arm artery. One or two fingers can be inserted between the rubber bag and the upper arm. In this case, the cuff is set so that the lower edge of the cuff is 2 or 3 cm from the elbow pocket. This is the standard or typical method of winding the cuff around the upper arm for blood pressure measurement.

This method is carried out directly by a doctor or a nurse for accurately measuring blood pressures; that is, the cuff is suitably wound on the upper arm directly by a doctor or a nurse. However, the method is not efficient when trained medical personnel are busy for medical examination, and especially in the case of mass physical examinations.

In order to eliminate this difficulty, a method has been proposed in which a cuff is wound along the inner wall of a cylinder and a person to be examined inserts his upper arm into the cuff thus wound. Air is fed into the rubber bag to inflate the cuff. However, this method is also disadvantageous in the following aspects. If the upper arm of a person to be examined is slender, then it is necessary to increase the quantity of air fed into the rubber bag, and at worst the surface of the upper arm is in circumferential line contact with the cuff surface. In this case, even if the cuff is pressurized to a level higher than the individuals maximum blood pressure, it is impossible to stop the circulation of blood.

Also, in the case of a slender arm, it is necessary to significantly inflate the rubber bag as described above, and therefore the rubber bag must be covered with a slackened fabric. Accordingly, during the process of gradually reducing the pressure to determine the systolic and diastolic blood pressures, the cuff greatly slackened is folded thereby generating noises. Since it is difficult to distinguish the noises thus generated from Korotkov sounds used to determine blood pressure points, this conventional method is liable to cause errors in blood pressure measurement.

In another conventional method, the cuff is wound around a part of the human body by means of an electric motor. However, the method is still disadvantageous in that a person to be examined may be uncomfortable because of the mechanized equipment. Furthermore, another conventional method is known in the art in which the squeezing force of the cuff is adjusted by driving an electric motor under the control of a control device. Such a method was disclosed in U.S. Pat. No. 3,935,984 issued Feb. 3, 1976. This method also involves problems. That is, if the control device is out of order or not satisfactorily functioning, the arm of a person to be examined may be excessively squeezed, with the result that the arm is damaged.

SUMMARY OF INVENTION

Accordingly, an object of this invention is to eliminate all of the above-described difficulties accompanying a conventional method.

More specifically, an object of the invention is to provide a device for automatically winding a blood pressure measuring cuff around a part of the human body, in which the cuff can be readily and quickly wound on a part of the human body.

Yet another object of this invention is to provide a device for winding a blood pressure measuring cuff wherein no excessively great winding force is needed, and a person to be examined will not be fearful or uncomfortable.

The foregoing objects and other objects of the invention are achieved by the provision of a device for automatically winding a blood pressure measuring cuff around a part of the human body. The cuff comprises a flexible band having a part fixedly secured to a surrounding member adapted to receive a part of the human body. The flexible band extends circumferentially along the inner wall of the surrounding member and has one end which is pulled circumferentially to be wound around a part of the human body. A flexible fluid chamber is provided along the inner wall of the flexible band to be interposed between the flexible band and a part of the human body, the flexible fluid chamber operating to apply a squeezing pressure to the part of the human body when a fluid is supplied to the flexible fluid chamber. A weight is connected to one end of the flexible band and weight hoisting means for hoisting the weight are employed. A weight holding means is used for holding the weight at a predetermined position and a pulling force caused by the weight when the holding of the weight is released is applied to the one end of the flexible band.

One embodiment of this invention will be described with reference to the accompanying drawings in detail.

BRIEF DESCRIPTION OF THE DRAWINGS

FIG. 1 is a schematic diagram showing the preferred embodiment of the invention;

FIG. 2 is a sectional view taken along line A—A in FIG. 1; and

FIG. 3 is a sectional view taken along line B—B in FIG. 1.

DESCRIPTION OF THE PREFERRED EMBODIMENT

As shown in FIGS. 1 through 3, an automatic cuff winding device comprises a flexible band assembly 1 (hereinafter referred to as "a cuff assembly 1" when applicable) and a weight operated cuff pulling device 20. The flexible band assembly 1 comprises a surrounding member 1A, a flexible band 4 (hereinafter referred to as "a cuff 4" when applicable), and a wire 6. The cuff 4 is cylindrically provided along the inner wall of the surrounding member 1A. The cuff has a fabric 17 which surrounds a flexible fluid chamber 3 over a leaf spring 2. The fabric 17, the flexible fluid chamber 3 and the leaf spring 2 form one unit. A part of the cuff 4 is clamped by an arm supporting board 5 provided on the surrounding member 1A. The cuff 4 has a free end 7. The other end of the cuff 4, wound more than one turn, is adapted as a connection 7A which is connected to one end of the wire 6. The other end of the wire 6, wound on the outer wall of the surrounding member 1A, is connected to the weight operated cuff pulling device 20. In FIG. 1, the dotted line 4A indicates the position of the cuff when wound around a part of the human body such as an arm, especially an upper arm, or a leg.

The weight operated cuff pulling device 20 comprises a wire winding drum 8 adapted to wind the wire 6 and a restoring spiral spring 9. An electromagnetic brake 10, electromagnetic clutches 11 and 12, a weight hoisting motor 13 and a weight hoisting drum 14 are all axially mounted. A weight 15, a weight holding solenoid 16, a limit switch 18, and a buffer device 19 complete the assembly. The weight 15 is provided with an engaging member 22 which is adapted to engage a pawl 21 coupled to the solenoid 16. In FIG. 1, the dotted line 15A indicates the weight dropped on the buffer 19 such as a dashpot or a spring.

The operation of the automatic cuff winding device thus organized will be described. In the cuff pulling device 20, the clutch 11 is released, and the clutch 12 is operated to drive the weight hoisting motor 13, in order to lift the weight 15A to a predetermined position. Upon operation of the motor 13, the drum 14 is rotated to hoist the weight 15. When the weight 15 reaches the predetermined position, and the engaging member 22 is brought into contact with the limit switch 18 to operate the switch. As a result, the solenoid which is energized is deenergized, whereupon the pawl 22 connected to the solenoid is engaged with the engaging member 22 thereby to hold the weight 15. When the weight 15 is held this manner, the electromagnetic clutch 12 is released to stop the motor 13.

Conversely, when the electromagnetic clutch 11 is released, the wire winding drum 8 is rotated to rewind the wire 6 by the restoring force of the restoring spiral spring 9 which has been wound by the weight dropping motion. As a result, the tension of the wire 6 is reduced, and the cuff 4 is restored as indicated by the solid lines in FIG. 1 by the restoring force of the leaf spring 2. Thus, the cuff 4 is ready again for being wound around, for instance, an upper arm.

For measuring blood pressure, the upper arm is inserted into the cuff 4 and is laid on the arm supporting board 5 of the surrounding member 1A. The electromagnetic clutch 11 is energized by operating a measurement start switch (not shown), as a result of which the electromagnetic brake 10 is released. When the weight holding solenoid is energized momentarily, the pawl 21 connected thereto is attracted to disengage from the engaging member 22 to permit the weight 15 to drop. The drum 14 is rotated by the weight dropping motion. The rotation of the drum 14 is transmitted through the electromagnetic clutch 11, the electromagnetic brake 10 and the restoring spiral spring 9 to the wire winding drum 8 to rotate drum 8. As a result, the wire connection 7A of the cuff 4 is pulled circumferentially by the wire 6 wound on the outer wall of the surrounding member 1A. Therefore, the cuff 4 is contracted in such a manner that the free end portion 7 having a contemplated length is inside while the wire connection 7A is outside. That is, the cuff 4 is wound on the upper arm supported on the arm supporting board similarly as in the case of bandaging an arm.

The force necessary for winding the cuff around the arm can be freely determined by suitably selecting the weight of the weight 15. Thus, a suitable force is applied to the cuff at all times. That is, no excessive pressure is applied to the cuff. Thus, the automatic cuff winding device is secured and can be applied to a patient without uneasiness.

A fluid such as air which is controlled by a supply valve connected to a fluid supply mechanism such as a fluid pump (not shown) is supplied to the flexible fluid chamber (rubber bag) 3 to inflate the latter 3. Because the leaf spring 2 is laid on the outer wall of the rubber bag 3, the rubber bag 3 is inflated substantially inwardly. As a result, the upper arm is further squeezed, and therefore the blood circulation is temporarily stopped. In this case, it is necessary to operate the electromagnetic brake 10 to stop the rotation of the drum 8 otherwise the wire winding drum 8 would be rotated reversely by the air pressure of the rubber bag 3 and the cuff 4 would be unwound.

A common sphygmomanometer is connected to the cuff 4 so that the expansion and contraction blood pressures of the heart are measured in a known manner. Upon completion of the measurement, the cuff pulling device is operated so that the dropped weight 15 is hoisted through the drum 14 by the motor 13. As a result, the flexible band assembly 1 releases the upper arm and it is placed in the preparation state as indicated by the solid lines in FIG. 1, ready for the next blood pressure measurement.

In the above-described embodiment of the invention, the cuff 4 comprises the fabric 17, with the leaf spring 2 surrounded by the fabric 17, and a rubber bag 3 provided along the inner wall of the leaf spring, as one unit. However, the arrangement of the cuff is not limited to the embodiment shown.

As is clear from the above description, according to the invention, the blood pressure measuring cuff is automatically wound around a part of the human body with the aid of the downward force of the weight. Accordingly, even when an accident occurs, no excessive pressure is applied to the part of the body. Furthermore, it is one of the significant merits of the invention that sounds, such as a motor drive sound which tends to make a patient mentally uncomfortable, will not occur during the cuff winding operation.

In the above-described embodiment, the cuff has the free end portion with the predetermined length held by the arm supporting board and the wire connection. The cuff is wound around a part of the human body, with a sufficient winding effect. Therefore, the cuff can be applied to any part of the human body irrespective of the size of the part. Since the cuff has no auxiliary instrument, such as for example an acoustic instrument, the cuff can be wound on either the right upper arm or the left upper arm.

What is claimed is:

1. Apparatus for automatically winding a blood pressure measuring cuff around a part of the human body, comprising; a flexible band having a part fixedly secured to a surrounding member adapted to receive a part of the human body, said flexible band extending circumferentially along the inner wall of said surrounding member, one end of said flexible band pulled circumferentially to be wound around a part of the human body, a flexible fluid chamber provided along the inner wall of said flexible band interposed between said flexible band and a part of the human body, a weight connected to one end of said flexible band, weight hoisting means for hoisting said weight and, weight holding means for holding said weight at a predetermined hoisting position, wherein a pulling force caused by said weight when said holding means is released is applied to the one end of said flexible band to wrap said flexible band about a part of the human body.

2. The apparatus of claim 1 wherein said weight hoisting means comprises a hoisting drum, a line wrapped about said drum and coupled to said weight and, motor means for rotating said drum.

3. The apparatus of claims 1 or 2 wherein said weight holding means comprises an engaging member mounted on said weight, and a solenoid having a pawl adapted to engage said engaging member.

4. The apparatus of claim 3 further comprising limit switch means to operate said solenoid when said weight reaches a predetermined position and to stop said weight hoisting means.

5. The apparatus of claims 1 or 2 wherein said weight is coupled to said one end of said flexible band by coupling means, said coupling means comprising a line wrapped about said surrounding member, one end of said line fixed to said surrounding member and the other end wrapped around a winding drum and, an axle extending through said winding drum and coupled to said weight hoisting means.

6. The apparatus of claim 5 further comprising clutch means disposed on said shaft between said winding drum and said weight hoisting means.

7. The apparatus of claim 5 further comprising a restoring spring mounted on said axle, said restoring spring biased in a direction opposite to the direction of winding drum rotation as said weight released and said flexible band is wrapped.

8. The apparatus of claim 1 wherein said part comprises a leaf spring disposed on the outside of said flexible bag and a cloth placed around the outside of said leaf spring.

* * * * *